(12) United States Patent
Shabazz

(10) Patent No.: US 6,352,690 B1
(45) Date of Patent: Mar. 5, 2002

(54) COMPOSITION FOR THE TREATMENT OF PSEUDOFOLLICULITIS BARBAE AND SKIN IRRITATION AND METHOD FOR THE APPLICATION THEREOF

(76) Inventor: Alfonso A. Shabazz, 300 W. North Ave., Chicago, IL (US) 60610

( * ) Notice: Subject to any disclaimer, the term of this patent is extended or adjusted under 35 U.S.C. 154(b) by 0 days.

(21) Appl. No.: 09/550,930

(22) Filed: Apr. 17, 2000

(51) Int. Cl.⁷ .............................. A61K 7/06; A61K 7/15
(52) U.S. Cl. ................... 424/73; 424/401; 424/DIG. 5; 514/944; 514/945; 514/789
(58) Field of Search ................... 424/73, 401

(56) References Cited

U.S. PATENT DOCUMENTS

| | | | |
|---|---|---|---|
| 4,421,739 A | 12/1983 | Bouillon et al. | 424/47 |
| 4,463,016 A | 7/1984 | Burgess | 424/347 |
| 4,867,967 A | 9/1989 | Cratcher | 424/80 |
| 5,034,221 A | 7/1991 | Rosen et al. | 424/73 |
| 5,435,997 A | 7/1995 | Burns | 424/73 |
| 5,976,547 A * | 11/1999 | Archer et al. | 424/195.1 |

* cited by examiner

*Primary Examiner*—James M. Spear
(74) *Attorney, Agent, or Firm*—Michael Best & Friedrich

(57) ABSTRACT

An effective and gentle formulation for the treatment and prevention of pseudofolliculitis barbae and skin irritation and method for the application of same is provided herein. In its preferred embodiment, the formulation consisting essentially of a petroleum balance containing 10% to 20% camphor, 5% fragrance oil and 1% to 2% mineral oil. The formulation is designed to prevent the razor bumps associated with pseudofolliculitis barbae without the use of harsh chemical compounds while allowing the user to continue to use a traditional method of shaving. The formulation is applied through a method consisting of shaving normally with a razor, application of a thin veneer of the formulation to the shaved area and removal of the formulation by means of a wet washcloth or other means.

11 Claims, No Drawings

_US 6,352,690 B1_

COMPOSITION FOR THE TREATMENT OF PSEUDOFOLLICULITIS BARBAE AND SKIN IRRITATION AND METHOD FOR THE APPLICATION THEREOF

FIELD OF THE INVENTION

The present invention relates generally to the treatment of pseudofolliculitis barbae and in the treatment and prevention of skin irritation. Specifically, the invention is a topical ointment designed to eliminate raised bumps and skin irritation that develops on the skin of some individuals after shaving. The compound is applied most preferably as a component of a cosmetically acceptable balm immediately after shaving.

BACKGROUND OF THE INVENTION

Pseudofolliculitis barbae is a common condition of the beard area occurring most often in African American men and other people with curly hair. The condition is commonly referred to as 'razor bumps'. The problem results when highly curved hairs grow back into the skin causing inflammation and a foreign body reaction. Over time, this can cause keloidal scarring which looks like hard bumps on the beard area and neck. Similar results can occur when other areas of the body are shaved, for example, the leg or underarm area.

Pseudofolliculitis barbae is a direct result of blade shaving. As an individual is shaving, the razor sharpens the ends of the hairs and the hairs then curve back into the individual's skin causing the body to react to the hair. Individuals who allow the affected hair to grow naturally normally do not experience razor bumps. However, some individuals choose not to allow the hair to grow. Also, some corporations have "no beard" policies which requires an individual to shave. Therefore, a treatment is needed to allow individuals who normally experience razor bumps to shave normally.

DESCRIPTION OF THE RELATED ART

Numerous compounds have been developed for the treatment of pseudofolliculitis barbae. These compounds, however, are different in chemical composition to the present invention. Further, the fact that pseudofolliculitis barbae is still a serious problem for many men and women is a clear indication that additional, more effective remedies are needed.

Some remedies for pseudofolliculitis barbae involve the application of depilatories. These depilatories use harsh chemicals to remove hair without shaving thereby preventing the curling of hair follicles and irritation. The depilatory compounds, however, are often unpleasant to use and can result in severe drying of the skin. Also, application of these products normally takes much longer than shaving with a razor.

Other chemical compounds have been designed to treat the user's skin after shaving with a standard razor and prevent pseudofolliculitis barbae. However, many of these compounds also contain harsh chemicals that may dry out the user's skin. See, for example, U.S. Pat. No. 5,435,997 which contains benzoyl peroxide, U.S. Pat. No. 4, 775,530 which contains alpha-hydroxy acid derivatives; and, U.S. Pat. No. 5,035,221 which contains acetylsalicylic acid and isopropyl alcohol. Repeated use of these chemical compounds can add additional irritation to the user. Further, the above patents have limited effectiveness eliminating pseudofolliculitis barbae.

The present treatment method overcomes the problems enumerated above.

SUMMARY OF THE INVENTION

The primary object of the present invention is to provide a simple, gentle and effective method for the treatment of pseudofolliculitis barbae which overcomes the disadvantages and limitations of the prior art.

It is an additional object of the present invention to provide treatment for shaved areas of the body while leaving the user's skin comfortable and soft.

It is an additional object of the invention to prevent pseudofolliculitis barbae within five days of beginning treatment with the compound.

In a preferred method of the invention, the compound comprises 10% camphor, 5% fragrance oil and 2% mineral oil thoroughly mixed in a petroleum balance.

Another object of the present invention is to treat skin irritation due primarily from shaving with a safety razor.

Another object of the present invention is to prevent skin irritation.

DETAILED DESCRIPTION OF THE INVENTION

The composition of the present invention applied topically for the treatment and prevention of pseudofolliculitis barbae and skin irritation caused by shaving with a safety razor. It has been discovered that the combination of three primary ingredients in a petrolatum base provides effective therapeutic action for the aforementioned conditions. The formulation is not harsh to the skin, causes no irritation and provides a soft texture to the skin without drying the skin.

An active ingredient in the composition is camphor, which may be present in amounts ranging from about 10% to about 20% of the total weight of the complete formulation. Camphor is a well known ingredient in topical formulations and is commonly used as an external analgesic. Camphor is a crystalline compound. In the present invention, it may be utilized as a crystal. Any source of camphor may be utilized in the composition as long as it is compatible with the carrier of the composition, a petroleum derived composition or any other, similar cosmetically acceptable suspension. The carrier may be petrolatum, or any other inert carrier that, as stated, any composition compatible with the ingredients that does not irritate the skin upon contact. The carrier is petrolatum balance or other cosmetically acceptable suspension, preferably, petrolatum and is used in amounts to fill the balance of the formulation. Preferably, the amounts range from about 84% to about 78% of the total weight of the formulation.

Another ingredient in the composition is a composition that emits a fragrance, for example, an oil. The fragrance oil may be musk oil, although other oils such as fruit or vegetable oils could be used. The oil must be compatible with the other ingredients and not be irritating to the skin. The fragrance oil may be present in the formulation in amounts ranging from about 5% to about 10% by weight of the composition.

Another ingredient in the formulation is an oil, preferably light mineral oil USP, or any other suitable oil. The oil provides lubricity to the formulation which results in a smooth soft texture when applied to the skin of the user. The mineral oil is present in the final formulation in amounts ranging from about 1% to about 2% of the formulation.

The formulation can be topically applied to the skin either immediately after shaving or once daily to treat and prevent skin irritation and pseudofolliculitis barbae. Of course, the formulation may be in many forms, a cream, gel, lotion, balm or sudsing agent. The foregoing formulation may be modified accordingly.

In preparing the formulation, solid pieces of camphor are placed in a small portion of light mineral oil USP until the camphor is wetted or moistened sufficiently so it can be crushed by hand with a pestle in a mortar. The pieces of camphor are preferably less than ½ inch long. It is preferably wetted with the oil for about 5 to about 10 minutes. It is ground to a relatively small size, approximately the size of granular white table sugar. More oil is added to mix the camphor particles until the particles are not visible by the unaided eye. A fragrance oil is added at this time. The solution of oils has a viscous soupy-like consistency.

Separately, the solid petrolatum USP, is heated sufficiently until it is liquid and then removed from the heat. While still liquid, the oil solution is added to the liquid petrolatum and blended to a smooth consistency. Containers may be filled with the product wherein the product is congealed at room temperature rendering a smooth salve.

The formulation of the present invention is used as follows:

1. Clean the area to be shaved.
2. Shave using a safety razor or other preferred method.
3. At the completion of the shave, use a warm compress to sooth the skin, and to cleanse excess debris from the shaved area.
4. Apply the product of the instant invention to the shaved area in a thin coat or veneer.
5. After a minute or two, use a moist cloth to gently wipe off the product of the instant invention.
6. Towel dry the shaved area.

The product of the instant invention may also be applied daily to any affected area regardless of shaving.

The product of the instant invention functions to treat or prevent pseudofolliculitis barbae, razor bumps, razor burns, sunburn or any other skin irritation. The formulation may also be applied by women for care under the arms and on legs to sooth the skin after shaving.

The following examples are illustrative of the formulation of the present invention and its method of use, but is not intended to limit its scope as claimed.

EXAMPLE I

Camphor weighing about 10 grams, was broken in relatively small pieces and wetted with light mineral oil USP in a mortar. It was allowed to set for about 5 minutes and ground with a pestle to a fine, granular particle size, approximately the size of white table sugar. The balance of the mineral oil, up to about 2 ml was added to the suspension and then mixed until the camphor granules are no longer visible to the unaided eye. Next, the fragrance oil, musk oil, is added in an amount of 5 ml. and the solution is mixed.

In a separate container about 83 gm of petrolatum USP is heated until it turns to liquid. The camphor solution is added and mixed into the liquid petrolatum thoroughly to provide a smooth, blended, viscous mixture. While still a liquid, containers are filled and the liquid salve is allowed to cool at room temperature for a few minutes to solidify.

EXAMPLE II

The product of the instant invention was compared with the product described in U.S. Pat. No. 5,435,997 (the '997 patent). The product of the '997 patent contains benzoyl peroxide (10%) in an amount of 75% with camphor in an amount of 05% and pure aloe vera in an amount of 20% by weight.

On day 1, three subjects, Mr. A, Mr. B, and Mr. S shaved their faces with safety razors and applied the product of the '997 patent immediately after shaving. Mr. A reported a stinging sensation, watering of the eyes, a pungent camphor odor and a tightening of the skin, as if an astringent had been applied to his shaved face. The subject washed the product off of his shaved face to avoid additional irritation.

Mr. B also reported stinging, watering of the eyes and a pungent camphor odor after the product of the '998 patent was applied to his shaven face. The subject washed the preparation from his face.

Mr. S applied the product of the '997 patent to his face after shaving. The subject noted an astringent feeling to the skin, a tightening of the skin and dryness.

On day 2, all subjects applied the product of the present invention to their respective shaved faces immediately after shaving. The product was allowed to stay on the shaved area for a brief period of time, about one minute, and then removed. All the subjects reported a soft, supple skin after the application of the present invention with no skin irritation and no drying of the skin.

While only a few, preferred embodiments of the invention have been described hereinabove, those of ordinary skill in the art will recognize that the embodiment may be modified and altered without departing from the central spirit and scope of the invention. Thus, the preferred embodiment described hereinabove is to be considered in all respects as illustrative and not restrictive, the scope of the invention being indicated by the appended claims, rather than by the foregoing description, and all changes which come within the meaning and range of equivalency of the claims are intended to be embraced herein.

What is claimed is:

1. A formulation for reducing the occurrence of and treatment of pseudofolliculitis barbae, said formulation consisting essentially of:
    about 10% camphor;
    about 10% fragrance oil;
    about 2% mineral oil,
    the remaining portion of the formulation consisting of a petroleum balance or other, similar cosmetically acceptable suspension.

2. A formulation for reducing the occurrence of and treatment of pseudofolliculitis barbae, said formulation consisting essentially of:
    approximately 10% to 20% camphor;
    approximately 5% to 10% fragrance oil;
    approximately 1% to 2% mineral oil,
    the remaining portion of the formulation consisting of a petroleum balance or other similar cosmetically acceptable suspension.

3. The formulation of claim 2 wherein the formulation is prepared as a gel, stick, foam or liquid.

4. The formulation of item 2 wherein the remaining portion is petrolatum.

5. A method for reducing the occurrence of and treatment of pseudofolliculitis barbae, said method comprising:
    shaving normally with a safety razor or other similar method; applying of a thin veneer to the shaved area a formulation consisting essentially of
    about 10% to 20% camphor, about 5% to 10% fragrance oil, about 1% to 2% mineral oil, the remaining portion of the formulation consisting of a petroleum balance or other similar cosmetically acceptable suspension.

6. The method of claim 5 wherein the remaining portion is petrolatum.

7. A formulation for reducing the occurrence of and treatment of skin irritation resulting from shaving consisting essentially of:

approximately 10% to 20% camphor;

approximately 5% to 10% fragrance oil;

approximately 1% to 2% mineral oil, the remaining portion of the formulation consisting of a petroleum balance or other similar cosmetically acceptable suspension.

8. The formulation of claim 7 wherein the remaining portion is petrolatum.

9. The formulation of claim 7 wherein the formulation is prepared as a gel, stick, foam or liquid.

10. A method for reducing the occurrence of and treatment of skin irritation resulting from shaving comprising:

shaving normally with a safety razor or other similar method;

applying of a thin veneer to the shaved area a formulation consisting essentially of about 10% to 20% camphor, about 5% to 10% fragrance oil, about 1% to 2% mineral oil; and the remaining portion of the formulation consisting of petroleum balance or other similar cosmetically acceptable suspension.

11. The method of claim 10 wherein the remaining portion is petrolatum.

* * * * *